(12) United States Patent
Yamada et al.

(10) Patent No.: US 6,221,638 B1
(45) Date of Patent: Apr. 24, 2001

(54) PROCESS FOR PRODUCING OPTICALLY ACTIVE AMINO COMPOUNDS

(75) Inventors: Yukio Yamada, Kakogawa; Akira Iwasaki, Akasahi; Noriyuki Kizaki, Takasago; Yasuhiro Ikenaka, Akashi; Masahiro Ogura, Ono; Junzo Hasegawa, Akashi, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/064,750

(22) Filed: Apr. 23, 1998

Related U.S. Application Data

(63) Continuation-in-part of application No. PCT/JP96/03054, filed on Oct. 21, 1996.

(30) Foreign Application Priority Data

Oct. 23, 1995 (JP) .................................. 7-299013

(51) Int. Cl.⁷ .................................................. C12P 13/00
(52) U.S. Cl. .......................................... 435/128; 435/830
(58) Field of Search ..................... 435/128, 830

(56) References Cited

U.S. PATENT DOCUMENTS

| | | | |
|---|---|---|---|
| 4,745,061 | * 5/1988 | Aretz et al. | 435/193 |
| 4,950,606 | 8/1990 | Stirling et al. | |
| 5,300,437 | * 4/1994 | Stirling et al. | 435/280 |
| 5,360,724 | 11/1994 | Matcham et al. | |

FOREIGN PATENT DOCUMENTS

| | | |
|---|---|---|
| 0135846A2 | 4/1985 | (EP) . |
| 91/05870 | * 5/1991 | (WO) . |

OTHER PUBLICATIONS

Lehninger, Biochemistry, Chapter 4, pp. 69–71 (1970).*
Bhatia et al., "Role Reversal for Substrates and Inhibitors", J. Biol. Chem. 268 (24) : 17687–94 (1993).*
Levashov, "Microheterogeneous surfactant–based systems as media for enzymatic reactions", Indian J. Chem., Sect. B 32B(1) : 167–9 (1993).*
Scheper et al., "A combination of selective mass transport and enzymatic reaction: enzyme immobilization in liquid surfactant", Ber. Bunsen–Ges. Phys. Chem. 93 (9) : 1034–8 (1989).*
Appl Microbiol Biotechnol (1990) 33:637–640, Asymmetric amination of 4–methoxyphenylacetone and its related compounds with microorganisms—Nakamichi et al.
Chemical Abstracts XP–002106436, Yorifuji et al., J. Biochem 1997, vol. 122 (3), pp. 537–543.

* cited by examiner

*Primary Examiner*—Sandra E. Saucier
(74) *Attorney, Agent, or Firm*—Birch, Stewart, Kolasch & Birch, LLP

(57) ABSTRACT

The method for preparing an optically active (R)-amino compound characterized by the method comprising stereoselectively carrying out amino group transfer by action of an (R)-form-specific transaminase in the co-presence of a ketone compound (amino acceptor), and an amino compound (amino donor) of a racemic form or an (R)-form, to give an optically active (R)-amino compound. According to the present invention, it is made possible to easily prepare at a high yield the optically active (R)-amino compounds and the like having an aryl group and the like at their 1-position, which have been conventionally difficult to prepare.

12 Claims, 2 Drawing Sheets

PROCESS FOR PRODUCING OPTICALLY ACTIVE AMINO COMPOUNDS

This application is a continuation-in-part application of PCT/JP96/03054 filed Oct. 21, 1996, the entire contents of which are incorporated herein by reference.

TECHNICAL FIELD

The present invention relates to optically active amino compounds having an aryl group and the like at the 1-position, which can be used as intermediates for pharmaceuticals and agricultural chemicals. 1-(3,4-Dimethoxyphenyl)-2-aminopropane, which is one of the desired compounds of the present invention, is an important compound as intermediates for CL316, 243 (J. D. Bloom et al., *J. Med. Chem.* 35, 3081–3084 (1992)) and analogous compounds thereof, which are promising as antidiabetics and agents for antiobesity under development.

In addition, (S)-2-amino-1-methoxypropane, which is another desired compound is a useful compound which can be used as intermediates for herbicides.

BACKGROUND ART

Processes for preparing optically active amino compounds having an aryl group and the like at the 1-position by using an enzyme include a report in Nakamichi et al. (*Appl. Microbiol. Biotechnol.*, 33, 634–640 (1990)) and Japanese Patent Examined Publication No. Hei 4-11194. It is disclosed in these publications that an (S)-form can be efficiently prepared by transferring an amino group to 1-(substituted phenyl)-2-propanones by using an enzyme. Further, Japanese Patent Examined Publication No. Hei 4-11194 also discloses a preparation of an (R)-form; however, the present inventors have conducted additional experiment to examine microorganisms and substrate disclosed in Japanese Patent Examined Publication No. Hei 4-11194 and found that the reproducibility by means of this method is very poor, and thereby making it difficult to use this method for practical purposes. Further, Stirling et al. disclose a method in which only the (S)-form is decomposed by actions of an ω-amino acid transaminase to a racemic amino compound produced by an organic reaction, to thereby obtain the remaining (R)-form (Japanese Patent Laid-Open No. Hei 3-103192). However, in this method, since the (S)-form is undesirably decomposed to obtain the (R)-form, the yield against the substrate is lowered to 50% or less. Accordingly, this method cannot be considered to be advantageous from the aspect of costs. In addition, Stirling et al., the authors as above, also disclose a method in which only (S)-amino compounds are prepared from a ketone-form by using an ω-amino acid transaminase in the presence of an amino donor. However, optically active (R)-amino compounds cannot be produced by this method.

DISCLOSURE OF INVENTION

Accordingly, an object of the present invention is to provide a method for preparing optically active (R)-amino compounds by actions of microbial enzymes efficiently and inexpensively.

The present inventors have found a microorganism from soil which can prepare optically active (R)-amino compounds with good yield by carrying out an amino group transfer to a ketone compound having an aryl group, and the like at 1-position (R)-form specifically and efficiently. This microorganism has been deposited at the National Institute of Bioscience and Human-Technology Agency of Industrial Science and Technology, located at 1-3, Higashi 1 chome Tsukuba-shi Ibaraki-ken 305, Japan, and has been given the depository designation number FERM BP-5228. Further studies have been made on the reaction using this microorganism, and the present invention has been completed.

Specifically, the present invention, in essence, pertains to:

[1] A method for preparing an optically active (R)-amino compound characterized by the method comprising stereoselectively carrying out amino group transfer by action of an (R)-form-specific transaminase in the co-presence of a ketone compound (amino acceptor) represented by the following general formula (I):

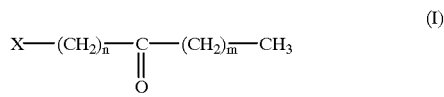
(I)

wherein n is 0 to 5; m is 0 or 1; and X represents an unsubstituted aryl group having 6 to 14 carbon atoms, an aryl group having 6 to 14 carbon atoms and having one or more substituents selected from the group consisting of an alkyl group having 4 to 15 carbon atoms, a hydroxyl group, a fluorine atom, a chlorine atom, a bromine atom, an iodine atom, a nitro group, a carboxyl group, and a trifluoromethyl group, or a methoxyl group, and an amino compound (amino donor) of an achiral form, a racemic form, or an (R)-form represented by the general formula (II):

(II)

wherein $X_1$ and $X_2$ independently represent a hydrogen atom; a straight-chain alkyl group having 1 to 10 carbon atoms; a branched alkyl group having 5 to 12 carbon atoms; an unsubstituted aryl group having 6 to 14 carbon atoms; an aryl group having 6 to 14 carbon atoms and having one or more substituents selected from the group consisting of an alkyl group having 1 to 4 carbon atoms, a hydroxyl group, a fluorine atom, a chlorine atom, a bromine atom, an iodine atom, a nitro group, and a carboxyl group; an aralkyl group having 7 to 16 carbon atoms and having one or more substituents selected from the group consisting of an alkyl group having 1 to 4 carbon atoms, a hydroxyl group, a fluorine atom, a chlorine atom, a bromine atom, an iodine atom, a nitro group, and a carboxyl group; or a hydroxymethyl group or a hydroxyethyl group, to give an optically active (R)-amino compound represented by the general formula (IV):

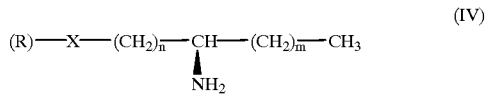
(IV)

wherein n, m, and X have the same definitions as those of n, m, and X in the general formula (I), respectively;

[2] The method for preparing an optically active (R)-amino compound described in item [1] above, characterized in that in the general formula (II), $X_1$ is an alkyl group having 2 to 10 carbon atoms, a phenyl group, or a naphthyl group, and $X_2$ is an alkyl group having 1 or 2 carbon atoms;

[3] The method for preparing an optically active (R)-amino compound described in item [1] above, characterized in that the amino donor represented by the general formula (II) is an alkyl ester of D-alanine, the alkyl group having 1 to 8 carbon atoms;

[4] The method for preparing an optically active (R)-amino compound described in item [1] above, wherein the amino donor represented by the general formula (II) is (R)-1-phenylethylamine, (R)-1-naphthylethylamine, (R)-1-methylpropylamine, (R)-2-aminopentane, (R)-2-amino-1-propanol, (R)-1-methylbutylamine, (R)-1-phenylmethylamine, (R)-1-amino-1-phenylethanol, (R)-2-amino-2-phenylethanol, (R)-3-aminoheptane, (R)-1-amino-3-phenylpropane, (R)-2-amino-4-phenylbutane, (R)-2-amino-3-phenylpropanol, (R)-3,4-dimethoxyaminopropane, (R)-1-methylheptylamine, benzylamine, (S)-2-phenylglycinol, 3-aminophenylbutane, L-phenylalaninol, (R)-2-amino-1-methoxypropane, D-alanine methyl ester, D-alanine ethyl ester, or a racemic compound thereof;

[5] The method for preparing an optically active (R)-amino compound described in any one of items [1] to [4] above, characterized in that in the general formula (I) and the general formula (IV), n and m are n=1 and m=0;

[6] The method for preparing an optically active (R)-amino compound described in any one of items [1] to [5] above, characterized in that in the general formula (I) and the general formula (IV), X is phenyl, 2-methoxyphenyl, 3-methoxyphenyl, 4-methoxyphenyl, 2,4-dimethoxyphenyl, 3,4-dimethoxyphenyl, 3-trifluoromethylphenyl, or methoxyl;

[7] The method for preparing an optically active (R)-amino compound described in any one of items [1] to [6] above, characterized in that the amino acceptor represented by the general formula (I) and the amino donor represented by the general formula (II) are brought into contact with a culture of microorganisms, separated bacterial cells, treated bacterial cells, or immobilized bacterial cells which produce (R)-form-specific transaminases;

[8] The method for preparing an optically active (R)-amino compound described in any one of items [1] to [6] above, characterized in that the amino acceptor represented by the general formula (I) and the amino donor represented by the general formula (II) are brought into contact with cell-free extracts of microorganisms, crudely purified enzymes, purified enzymes, or immobilized enzymes which produce (R)-form-specific transaminases;

[9] The method for preparing an optically active (R)-amino compound described in any one of items [1] to [8] above, wherein the microorganism for producing the transaminase is a microorganism belonging to the genus Arthrobacter;

[10] The method for preparing an optically active (R)-amino compound described in item [9] above, wherein the microorganism belonging to the genus Arthrobacter is Arthrobacter species (Arthrobacter sp.) KNK168 (FERM BP-5228);

[11] The method for preparing an optically active (R)-amino compound described in any one of items [1] to [10] above, characterized by adding to a medium, when culturing the microorganism for producing the transaminase, one or more members selected from the group consisting of (RS)-1-methylpropylamine, (RS)-1-phenylethylamine, (RS)-1-methylbutylamine, (RS)-3-amino-2,2-dimethylbutane, (RS)-2-amino-1-butanol, and (R)- or (RS)-1-(3,4-dimethoxyphenyl)aminopropane as an inducer for the enzyme;

[12] The method for preparing an optically active (R)-amino compound described in item [1] above, characterized by carrying out the reaction at a pH of not less than 5 and not more than 12 in the amino group transfer reaction;

[13] The method for preparing an optically active (R)-amino compound described in item [1] above, characterized by adding a surfactant or a fatty acid as a reaction accelerator upon reaction in the amino group transfer reaction;

[14] A method for preparing an optically active (S)-amino compound, characterized by the method comprising stereoselectively carrying out amino group transfer reaction by action of an (R)-form-specific transaminase to an amino compound of a racemic form represented by the general formula (V) in the presence of a ketone compound (amino acceptor) represented by the general formula (III), to give an optically active (S)-amino compound represented by the general formula (VI).

$$\underset{X_2}{\overset{X_1}{>}}=O \quad \text{(III)}$$

$$(RS)-X-(CH_2)_{\overline{n}}-\underset{NH_2}{\overset{H}{\underset{|}{C}}}-(CH_2)_{\overline{m}}-CH_3 \quad \text{(V)}$$

$$(S)-X-(CH_2)_{\overline{n}}-\underset{NH_2}{\overset{H}{\underset{|}{C}}}-(CH_2)_{\overline{m}}-CH_3 \quad \text{(VI)}$$

[15] An (R)-form-specific transaminase obtainable from a culture of a microorganism belonging to the genus Arthrobacter; and

[16] The (R)-form-specific transaminase described in item [15] above, wherein the transaminase contains an amino acid sequence of:
Glu-Ile-Val-Tyr-Thr-His-Asp-Thr-Gly-Leu-Asp-Tyr (SEQ ID NO:1) in the neighborhood of an amino terminal of the enzyme protein.

BEST MODE FOR CARRYING OUT THE INVENTION

Figure 1:
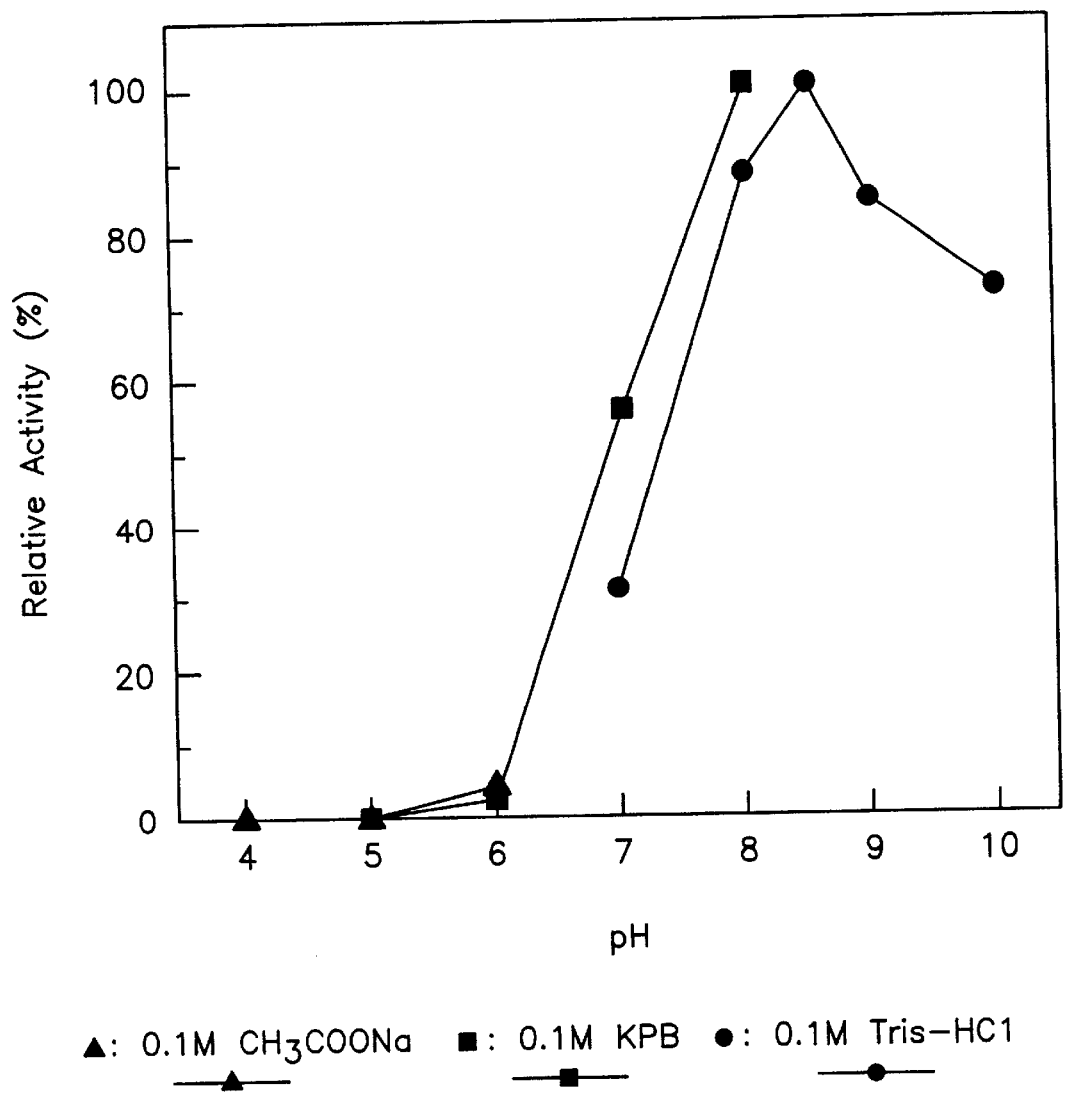
FIG. 1 is a graph showing the optimal pH for the enzyme of the present invention.

The present invention will be described in detail below. First, the reaction scheme in the present invention is shown as follows.

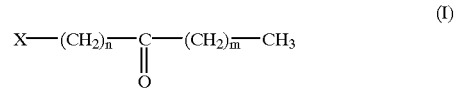

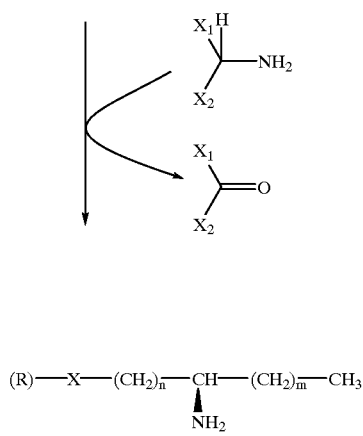

(R)—X—(CH$_2$)$_n$—CH—(CH$_2$)$_m$—CH$_3$    (IV)
                                  |
                                 NH$_2$

The present inventors have carried out repeated screening to separate bacteria from domestic soil which have an ability of producing (R)-amino compounds in (R)-form selectivity using ketones as substrates, and consequently have found that bacteria belonging to the genus Arthrobacter have strong activity for catalyzing this reaction. Among them, the bacteriological natures of Arthrobacter sp. KNK168 (FERM BP-5228), a typical example thereof, are shown as follows.

| | |
|---|---|
| Cell Morphology | Rod (Coryne type) |
| Gram Staining | Positive |
| Spore Formation | None |
| Motility | None |
| Colony Morphology | Round, regular, entire, yellow, smooth, glossy, semi-translucent, convex, 2 m in diameter (Bennett's agar medium) |
| Growth (30° C.) | + |
| (37° C.) | − |
| Catalase | + |
| Oxidase | − |
| OF Test (glucose) | − (oxidative) |
| Cell Wall | No mycolic acid; diamino acid is lysine. |
| Fatty Acid Analysis | Almost all the acids present are three-branched iso and anteiso acid. |

From the aspects that an (R)-form amine, such as (R)-1-phenylethylamine, is used as an amino donor and that the resulting product is an optically active (R)-amino compound as described in detail below, the transaminase produced by this bacterium is obviously different from an enzyme of Brevibacterium linens IFO12141 used in Nakamichi et al. (Appl. Microbiol. Biotechnol., 33, 634–640 (1990)) and an ω-amino acid transaminase used in Stirling et al. (Japanese Patent Laid-Open No. Hei 3-103192), in which an (S)-amine is used as an amino donor and the resulting product is an optically active (S)-amino compound.

Further, the transaminase derived from Arthrobacter which can be used in the present invention is different from the above-mentioned enzyme derived from Brevibacterium in many other aspects. For example, there are differences from the aspect that inorganic ammonium salts such as ammonium chloride, and L-amino acids (being (S)-amines) such as glutamic acid and aspartic acid cannot be used as an amino donor (Table 1).

TABLE 1

| Amino Group Donor | Transaminase of Present Invention | Enzyme Used in Nakamichi et al. |
|---|---|---|
| Inorganic Ammonium Salt | − | + |
| L-Amino Acid | − | + |

In addition, when the transaminase derived from Arthrobacter which can be used in the present invention is compared with the ω-amino acid transaminase used in Stirling et al. (Japanese Patent Laid-Open No. Hei 3-103192), in addition to the obvious difference regarding the above-mentioned substrate specificity, there are differences from the aspect that the transaminase derived from Arthrobacter does not act to ω-amino acids such as β-alanine and 4-aminobutyric acid, and ω-amines such as n-butylamine and putrescine, and DL-3-aminobutyric acid, and the like, and that the transaminase derived from Arthrobacter is affected only a little by reaction inhibitors such as hydroxylamine and phenylhydrazine.

In addition, as other enzymes similar to the enzyme used by the present inventors, benzylamine transaminase is disclosed in Okada et al. (Japanese Patent Laid-Open No. Hei 6-178685), wherein the benzylamine transaminase strongly acts to benzylamine in the presence of pyruvic acid to form L-alanine and benzaldehyde. However, the benzylamine transaminase has a similar optical specificity to that of the above-mentioned enzyme derived from Brevibacterium or to that of the ω-amino acid transaminase from the aspect that the optical activity of the product by the transaminase action of this enzyme is that of L-alanine of an (S)-form, and it can be said that the benzylamine transaminase is completely different from the enzyme derived from Arthrobacter which can be used in the present invention.

Further, when these enzymes are compared, it seems that there are some differences in influence caused by reaction inhibitors such as phenylhydrazine, D-penicillamine, and p-chloromercuribenzoic acid.

The differences with the ω-amino acid transaminase derived from Pseudomonas sp. F-1 (Agric. Biol. Chem., 42, 2363–2367 (1978), Agric. Biol. Chem., 43, 1043–1048 (1979), J. Biol. Chem., 258, 2260–2265 (1983)) which have been well studied among the ω-amino acid transaminases, and with the benzylamine transaminase of Okada et al. (Japanese Patent Laid-Open No. Hei 6-178685) are summarized and shown in Table 2. In a case of the transaminase action in the present invention, the data of the purified enzyme are used, and in cases of those by other two enzymes, the data of the purified enzymes which are disclosed in each of the literature publication and patent publication are used. Pyruvic acid is used as an amino acceptor in all cases.

TABLE 2

| Substrate Specificity | Transaminase of Present Invention (Relative Activity: %) | ω-Amino Acid Transaminase (Relative Activity: %) | Transaminase of Okada et al. (Relative Activity: %) |
|---|---|---|---|
| β-Alanine | 0 | 100 | 0 |
| 4-Aminobutyric acid | 0 | 40 | |
| DL-3-Aminobutyric acid | 0 | 96 | |
| n-Butylamine | 0 | 60 | 0 |
| Benzylamine | 0.8 | 45 | 100 |
| Putrescine | 0 | 55 | 0 |
| β-Phenethylamine | 0 | 54 | 9 |
| Amino Group Donor | | | |
| L-Alanine | — | + | + |
| Inhibitor (1 mM each) | (Relative Activity: %) | (Relative Activity: %) | (Relative Activity: %) |
| (without addition) | 100 | 100 | 100 |
| Hydroxylamine | 17 | 0 | 30 (0.1 mM) |
| Phenylhydrazine | 82 | 6 | 27 |
| D-Penicillamine | 93 | 65 | 0 |
| p-Chloromercuri-benzoic acid | 53 | 100 | 9 (0.1 mM) |
| CuSO$_4$ | 44 | | 5 (0.5 mM) |
| Gabaculine | 24 | 0 | |

The activity of the transaminase (intracellular enzyme) which can be used in the present invention against the typical substrates of the (ω-aminotransferases is shown in Table 3. In the case of using an ω-amino acid or an ω-amine as an amino donor, the ω-aminotransferase activity is extremely low, and the transferase used in the present invention does not act to β-alanine which is a typical substrate of ω-amino acid-pyruvic acid aminotransferase. The transferase used in the present invention shows an especially high activity to (R)-1-phenylethylamine. Therefore, it is quite different from the ω-amino transaminase in the substrate specificity.

TABLE 3

| Amino Donor | Amino Acceptor | Relative Activity (%) |
|---|---|---|
| β-Alanine | Pyruvic acid | 0 |
| 4-Aminobutyric acid | 2-Ketoglutaric acid | 0 |
| 2,5-Diaminovalerate (α,ω-amino acid) | 2-Ketoglutaric acid | 2 |
| DL-Ornithine | 2-Ketoglutaric acid | 0 |
| DL-Lysine | 2-Ketoglutaric acid | 0 |
| Putrescine (α,ω-Diamine) | 2-Ketoglutaric acid | 0 |
| α-2,4-Diaminobutyric acid | Pyruvic acid | 0 |
| Taurine | 2-Ketoglutaric acid | 0 |
| DL-Asparagine | 2-Ketoglutaric acid | 0 |
| DL-Glutamine | 2-Ketoglutaric acid | 0 |
| (R)-1-Phenylethylamine | Pyruvic acid | 100 (Control) |

The (R)-form-specific transaminase produced by Arthrobacter species (Arthrobacter sp.) KNK168 (FERM BP-5228) used in the present invention has an amino acid sequence of SEQ ID NO:1 in Sequence Listing:

Glu-Ile-Val-Tyr-Thr-His-Asp-Thr-Gly-Leu-Asp-Tyr in the neighborhood of an amino terminal of the enzyme protein.

In a case where the amino group transfer action which can be used in the present invention is carried out, the enzymatic activity is increased by addition of an inducer upon culturing microorganisms. The above inducers include one or more members of amines, such as (RS)-1-methylpropylamine, (RS)-1-phenylethylamine, (RS)-1-methylbutylamine, (RS)-3-amino-2,2-dimethylbutane, (RS)-2-amino-1-butanol, and (R)- or (RS)-1-(3,4-dimethoxyphenyl)aminopropane.

The transaminase derived from Arthrobacter which can be used in the present invention can be used in various forms. In other words, not only cultured microorganisms, separated bacterial cells and treated bacterial cells, but also cell-free extracts, crudely purified enzymes, purified enzymes, and the like can be used. Further, immobilized products of these cells, immobilized products of the treated bacterial cells, immobilized products of enzyme proteins to immobilizing carriers (for example, anionic exchange resins) and the like can be also used. Here, the immobilization can be carried out by conventional methods (for example, Japanese Patent Laid-Open No. Sho 63-185382).

Supporting materials which can be used in the immobilization include various kinds of anionic exchange resins, such as various amines, ammonium salts and diethanolamine type resins having functional groups. Suitable examples thereof include phenol-formaldehyde anionic exchange resins such as Duolite A568 and DS17186 (registered trademark of Rohm and Haas Company); polystyrene resins, such as Amberlite IRA935, IRA945, and IRA901 (registered trademark of Rohm and Haas Company), Lewatit OC1037 (registered trademark of Bayer A. G.), and Diaion EX-05 (registered trademark of MITSUBISHI KASEI CORPORATION), and the like. In addition, supporting materials, such as DEAE-cellulose, can be used.

Further, cross-linking agents are usually used in order to make the adsorption of enzyme more firm and stable. A preferable example of the cross-linking agents includes glutaraldehyde. The enzymes used include purified enzymes, as well as enzymes at various levels of the purification, such as partially purified enzymes, solutions of disrupted cells, and cell-free extracts.

As a preparation method of the immobilized enzyme, conventional preparation methods may be employed, including, for example, a method wherein the cross-linking treatment is carried out after adsorption of an enzyme to a supporting material.

In other words, in the present invention, it is preferable that the amino acceptor represented by the general formula (I) and the amino donor represented by the general formula (II) are brought into contact to a culture of microorganisms, separated bacterial cells, treated bacterial cells, or immobilized bacterial cells which produce (R)-form-specific transaminase, or into contact to cell-free extracts of microorganisms, crudely purified enzymes, purified enzymes, or immobilized enzymes which produce (R)-form-specific transaminases.

The amino acceptors which can be used in the present invention include ketones represented by the general formula (I). In the formula, n is 0 to 5; m is 0 or 1; and X represents an unsubstituted aryl group having 6 to 14 carbon atoms, an aryl group having 6 to 14 carbon atoms and having one or more substituents selected from the group consisting of an alkyl group having 4 to 15 carbon atoms, a hydroxyl group, a fluorine atom, a chlorine atom, a bromine atom, an iodine atom, a nitro group, a carboxyl group, and a trifluoromethyl group, or a methoxy group.

Among them, a compound with n=1 and m=0, for example, 1-aryl-2-propanone or 1-methoxy-2-propanone, is preferable. In addition, the compound in which the aryl group is a phenyl group, a 2-methoxyphenyl group, a 3-methoxyphenyl group, a 4-methoxyphenyl group, a 2,4-dimethoxyphenyl group, a 3,4-dimethoxyphenyl group, or a 3-trifluoromethylphenyl group is also preferable.

The amino donors used in the present invention include amino compounds represented by the general formula (II) of an achiral form, a racemic form, or an (R)-form. In the general formula (II), $X_1$ and $X_2$ independently represent a hydrogen atom; a straight-chain alkyl group having 1 to 10 carbon atoms; a branched alkyl group having 5 to 12 carbon atoms; an unsubstituted aryl group having 6 to 14 carbon atoms; an aryl group having 6 to 14 carbon atoms having one or more substituents selected from the group consisting of an alkyl group having 1 to 4 carbon atoms, a hydroxyl group, a fluorine atom, a chlorine atom, a bromine atom, an iodine atom, a nitro group, and a carboxyl group; an aralkyl group having 7 to 16 carbon atoms and having one or more substituents selected from the group consisting of an alkyl group having 1 to 4 carbon atoms, a hydroxyl group, a fluorine atom, a chlorine atom, a bromine atom, an iodine atom, a nitro group, and a carboxyl group; or a hydroxymethyl group or a hydroxyethyl group.

Among the above-mentioned amines, amines in which $X_1$ is an alkyl group having 2 to 10 carbon atoms, a phenyl group or a naphthyl group, and $X_2$ is an alkyl group having 1 or 2 carbon atoms, or alkyl esters of D-alanine, the alkyl group having 1 to 8 carbon atoms, are particularly preferable. Concrete examples of the amines include, for instance, (R)-1-phenylethylamine, (R)-1-naphthylethylamine, (R)-1-methylpropylamine, (R)-2-aminopentane, (R)-2-amino-1-propanol, (R)-1-methylbutylamine, (R)-1-phenylmethylamine, (R)-1-amino-1-phenylethanol, (R)-2-amino-2-phenylethanol, (R)-3-aminoheptane, (R)-1-amino-3-phenylpropane, (R)-2-amino-4-phenylbutane, (R)-2-amino-3-phenylpropanol, (R)-3,4-dimethoxyaminopropane, (R)-1-methylheptylamine, benzylamine, (S)-2-phenylglycinol, 3-aminophenylbutane, L-phenylalaninol, (R)-2-amino-1-methoxypropane, D-alanine methyl ester, D-alanine ethyl ester, and the like.

The concentrations of the substrates used in the reaction are as follows. It is preferred that the concentration of the amino acceptor is from 0.1 to 10%, preferably from 3 to 5%. Regarding the concentration of the amino donor, it is preferred that the concentration of an (R)-form, in the case of chiral amine, is about 80 to 150 mol % to the amino acceptor. In addition, racemic amino compounds can be also used as amino donors. In such cases, however, twice the concentration as that of the (R)-form is needed.

The pH during the reaction is usually a pH of from 5.0 to 12.0, preferably a pH of from 7.0 to 10.0. The temperature during the reaction is usually from 25° to 40° C., preferably from 30° to 35° C.

Further, the yield of reaction may be increased by adding a surfactant, including sodium dodecyl sulfate (SDS), Triton X-100, cetyl trimethylammonium bromide (CTAB), or the like, or a fatty acid, including linoleic acid, oleic acid, or the like, in an amount of from 0.1 to 10%.

The optically active amino compounds which are prepared by the method of the present invention are the (R)-amino compounds represented by the general formula (IV). In the formula, n, m, and X, respectively, has the same definitions as those in the general formula (I).

Concrete examples of the compounds include, for instance,
(R)-1-phenyl-2-aminopropane,
(R)-1-phenyl-3-aminobutane,
(R)-1-(3,4-dimethoxyphenyl)-2-aminopropane,
(R)-3-(trifluoromethylphenyl)-2-aminopropane,
(R)-3-(p-methoxyphenyl)-2-aminopropane,
(R)-4-(p-methoxyphenyl)-2-aminobutane,
(R)-4-(3',4'-methylenedioxyphenyl)-2-aminobutane, (R)-4-(p-hydroxyphenyl)-2-aminobutane,
(R)-1-(3-trifluoromethylphenyl)-2-aminopropane,
(R)-2-amino-1-methoxypropane, and the like.

By the preparation method of the present invention, for example, in a case where 1-(3,4-dimethoxyphenyl)-2-propanone used as an amino acceptor and (R)-1-phenylethylamine used as an amino donor, each having a concentration of 3%, are reacted by using Arthrobacter species KNK168 (FERM BP-5228) for about 20 hours, 75% or more of 1-(3,4-dimethoxyphenyl)-2-propanone can be converted to (R)-1-(3,4-dimethoxyphenyl)-2-aminopropane with an optical purity of 99% ee or more by the amino group transfer action.

The quantitative analysis of the optically active amino compound obtained as the reaction product can be carried out by means of high-performance liquid chromatography. For example, the quantitative analysis can be carried out by separating the reaction mixture by using a reversed phase column (Cosmosil $5C_{18}$-AR, NACALAI TESQUE, INC., and the like) and using 25% acetonitrile as a moving phase, and the detected absorptions at 210 nm were compared with the control. In addition, there are several methods for measuring the optical purity. For example, the analysis of the optical purity can be carried out by binding the resulting optically active amino compound to N-carboxy-L-leucine anhydride, and the like, in order to form a diastereomer, and thereafter separating and quantitatively analyzing this diastereomer by the above-mentioned high-performance liquid chromatography method.

The method for separating the optically active amino compound, the desired compound, after the reaction can be carried out by the conventional method in which extraction by an organic solvent and distillation are combinably used. For example, ethyl acetate, toluene, and the like can be used as the extraction solvent. First, the reaction solution is made acidic and the ketones are removed therefrom by extraction. Thereafter, the reaction mixture is made alkaline, and separate the amines including the desired compound by extraction. Further, by further means of distillation of the extracted fraction, the desired optically active amino compound can be isolated.

In the transaminase which can be used in the present invention, when acted the racemic amino compound represented by the general formula (V) in the presence of the ketone compound (amino acceptor) represented by the general formula (III), only its (R)-form is selectively converted to ketone compounds, because the transaminase only acts to the (R)-form, so that the (S)-form remains unchanged, and thus, collected as the amino compound. Therefore, the (S)-amino compounds represented by the general formula (VI) can be easily prepared from racemic amino compounds by using the transaminase of the present invention.

For example, in a case where racemic forms of 1-(3,4-dimethoxyphenyl)-2-aminopropane or 2-amino-1-methoxypropane are reacted with pyruvic acid used as an amino acceptor using Arthrobacter species KNK168 (FERM BP-5228), the (R)-form amino compound is converted to the ketone form by the amino group transfer, so that the (S)-form amino compound can be obtained at about 50% yield in a concentrated state up to a high optical purity level.

The present invention will be described in further detail by means of the working examples, but the scope of the present invention is by no means limited to these examples.

EXAMPLE 1

Each 2 g of soil samples collected at various places in this country was suspended in 5 ml of physiological saline. 0.2 ml of the supernatant thereof was added to 4 ml of an S medium (2 g/L $KH_2PO_4$, 2 g/L $K_2HPO_4$, 0.3 g/L $MgSO_4 \cdot 7H_2O$, 5 g/L glycerol, 3 g/L NaCl, 1 g/L yeast extract powder, 0.004 g/L $FeSO_4 \cdot 7H_2O$, 0.0005 g/L $ZnSO_4 \cdot 7H_2O$, 0.0005 g/L $MnCl_2 \cdot 4H_2O$ (pH 7.5); and 2-oxoglutaric acid or pyruvic acid, filtrated by a microorganisms exclusion filter after a treatment of autoclaving, and (R)-1-(3,4-dimethoxyphenyl)-2-aminopropane being added so as to give final concentrations of 1.5 g/L and 1.0 g/L, respectively). The resulting culture was subjected to an enrichment culture at 30° C. for 3 to 7 days. Each 0.2 ml of the culture in which the bacteria were grown was spread on an S-medium plate containing 1.5% of agar, and the colonies were grown by culturing at 30° C. The grown colonies were subjected to shaking culture in the S-medium. After harvesting the cells, they were suspended in 0.25 ml of a reaction mixture containing a 0.1 M carbonic acid buffer (pH 8.5), 50 mM pyruvic acid and 30 mM (R)-1-(3,4-dimethoxyphenyl)-2-aminopropane, and the components were reacted with stirring at 30° C. for 24 hours.

The resulting reaction mixture was separated by thin-layer chromatography (Kieselgel 60F254 (Merck); developing solvent being diethyl ether:methanol:aqueous ammonia solution (27%)=50:50:2). The decrease of the substrates was detected by ninhydrin, and the formation of the resulting product, 1-(3,4-dimethoxyphenyl)-2-propanone, was detected by 0.4% of 2,4-dihydrophenyl hydrazine. With regard to the strains in which the formation of the products was confirmed, the presence or absence of the (R)-form-specific amino group transfer action activity was examined by carrying out its reverse reaction. Specifically, the cultured cells were added to a reaction mixture containing 0.6% of 1-(3,4-dimethoxyphenyl)-2-propanone and 0.6% of (R)-1-phenylethylamine, and the components were reacted at 30° C. for 2 days. As a result, the Arthrobacter species KNK168 strain was found to have the (R)-form-specific amino group transfer activity.

EXAMPLE 2

When culturing the Arthrobacter species KNK168 strain by the method described in Example 1, (RS)-1-methylpropylamine, (RS)-1-methylbutylamine, (RS)-3-amino-2,2-dimethylbutane, (RS)-2-amino-1-butanol, or (RS)-1-phenylethylamine was added to the medium in place of (R)-1-(3,4-dimethoxyphenyl)-2-aminopropane ((R)-DMA). The cells were separated from the medium, and the reaction was carried out at 30° C. for 20 hours using the above cells in a reaction mixture containing 1% of 1-(3,4-dimethoxyphenyl)-2-propanone and 1% of (RS)-1-methylpropylamine. As a result, an increase of the reactivity was observed as shown in Table 4.

TABLE 4

| Inducer | (R)-DMA Formed (%) |
| --- | --- |
| (RS)-1-Methylpropylamine | 22.3 |
| (RS)-1-Methylbutylamine | 13.0 |
| (RS)-1-Phenylethylamine | 8.0 |
| (RS)-3-Amino-2,2-dimethylbutane | 18.6 |
| (RS)-2-Amino-1-butanol | 12.9 |
| (R)-DMA | 0.9 |
| No Addition | 0.3 |

EXAMPLE 3

The Arthrobacter species KNK168 strain was inoculated to an R medium (5 g/L $KH_2PO_4$, 5 g/L $K_2HPO_4$, 3 g/L NaCl, 1 g/L $MgSO_4 \cdot 7H_2O$, 0.005 g/L $FeSO_4 \cdot 7H_2O$, 0.001 g/L $ZnSO_4 \cdot 7H_2O$, 0.001 g/L $MnCl_2 \cdot 4H_2O$ (pH 7.5), 15 g/L glycerol, 2 g/L yeast extract powder, 8 g/L PRO-EX (BANSYU CHOMIRYO CO., LTD.); pyruvic acid, filtrated by a microorganisms exclusion filter after a treatment of autoclaving, and (RS)-1-methylpropylamine being added so as to give final concentrations of 1.6 g/L and 2.0 g/L, respectively, and being adjusted to pH 7.2), and then subjected to shaking culture at 30° C. for 24 hours. The cultured cells were harvested by centrifugation, and the harvested cells were suspended in a reaction mixture (pH 8.5) containing 1% of 1-(3,4-dimethoxyphenyl)-2-propanone, 0.1% of Triton X-100, and 1% of an amino donor shown in Table 2. The components were reacted at 35° C. for 20 hours. As shown in Table 5, it was found that (RS)-1-phenylethylamine, (RS)-1-methylbutylamine, (RS)-1-methylpropylamine, (RS)-2-aminopentane, and the like, functioned as amino donors, among which (RS)-1-phenylethylamine was most highly preferable.

TABLE 5

| Amino Group Donor | (R)-DMA Formed (%) |
| --- | --- |
| (RS)-1-Phenylethylamine | 61.3 |
| (RS)-1-Methylbutylamine | 54.7 |
| (RS)-1-Methylpropylamine | 28.2 |
| (RS)-2-Aminopentane | 56.9 |
| (RS)-2-Amino-1-propanol | 9.6 |
| (RS)-2-Amino-2-phenylethanol | 48.4 |
| (RS)-2-Amino-3-phenylpropanol | 22.7 |
| (RS)-2-Amino-4-phenylbutane | 27.6 |
| (RS)-1-Amino-2-phenylpropane | 1.8 |
| (RS)-1-Phenylmethylamine | 3.1 |
| (RS)-3-Aminoheptane | 7.4 |
| (RS)-1-Naphthylethylamine | 34.2 |
| D-Alanine methyl ester | 3.5 |
| D-Alanine ethyl ester | 4.2 |
| D-Alanine | 3.0 |

EXAMPLE 4

The cells obtained by culturing the Arthrobacter species KNK168 strain in the R medium were suspended in a reaction mixture containing 2% of 1-(3,4-dimethoxyphenyl)-2-propanone and 4% of (RS)-1-phenylethylamine. The surfactants and fatty acids shown in Table 6 were added thereto, and the mixture was reacted at 30° C. at a pH of 8.5 for 20 hours. As a result, it was found that the rate of reaction was increased by addition of sodium dodecyl sulfate, linoleic acid, oleic acid, or the like to the reaction mixture.

TABLE 6

| Additives (%) | | (R)-DMA Formed (%) |
|---|---|---|
| Triton X-100 | 0.1 | 31.6 |
| | 0.5 | 34.0 |
| Sodium dodecyl sulfate | 0.1 | 45.3 |
| | 0.5 | 42.2 |
| | 1.0 | 46.3 |
| | 2.0 | 50.1 |
| | 3.0 | 51.9 |
| | 4.0 | 53.1 |
| Cetyl trimethyl ammonium bromide (CTAB) | 0.1 | 29.1 |
| Linoleic Acid | 2.9 | 45.1 |
| Oleic Acid | 2.9 | 44.9 |
| (No Addition) | | 28.1 |

EXAMPLE 5

Using the cells obtained by culturing the Arthrobacter species KNK168 strain in the R medium, the components were reacted at 35° C. for 20 hours, while making the pH of a reaction mixture variable from 7.5 to 9.5, the reaction mixture containing 2% of 1-(3,4-dimethoxyphenyl)-2-propanone, 1.4% of (RS)-1-phenylethylamine, and 0.1% of sodium dodecyl sulfate. As a result, the rate of reaction at a pH of 8.5 to 9.0 was favorable as shown in Table 7.

TABLE 7

| Reaction pH | (R)-DMA Formed (%) |
|---|---|
| 7.5 | 16.8 |
| 8.0 | 30.8 |
| 8.5 | 40.0 |
| 9.0 | 41.6 |
| 9.5 | 36.1 |

EXAMPLE 6

30 ml of overnight preculture of the Arthrobacter species KNK168 strain was inoculated to 1.5 liter of a J medium (5 g/L KH$_2$PO$_4$, 5 g/L K$_2$HPO$_4$, 1 g/L NaCl, 1 g/L MgSO$_4$.7H$_2$O, 0.005 g/L FeSO$_4$.7H$_2$O, 0.001 g/L ZnSO$_4$.7H$_2$O, 0.001 g/L MnCl$_2$.4H$_2$O, 0.0005 g/L CuSO$_4$.5H$_2$O (pH 7.5), 40 g/L glycerol, 3 g/L yeast extract powder, 20 g/L PRO-EX (BANSYU CHOMIRYO CO., LTD.), a pH being adjusted to 7.5) in a 2 liter-mini jar, and the bacterium was cultured at 30° C. at 0.5 vvm at 450 rpm for 43 hours while keeping and adjusting the culture to a pH of 7.5. Incidentally, from the start of culturing, (RS)-1-methylpropylamine filtered by a microorganisms exclusion filter was added so as to have a final concentration of 4 g/L after 14 hours. The final cell concentration (OD$_{610}$) was about 29 at the end of the culture, and the transaminase activity was 0.3 unit per the culture at that time. Incidentally, the unit of enzymatic activity means the intensity of the enzymatic activity which converts a 1 μM substrate of 1-(3,4-dimethoxyphenyl)-2-propanone to (R)-1-(3,4-dimethoxyphenyl)-2-aminopropane at 30° C. in 1 minute.

The cells harvested from 1.5 liter of the culture were suspended in a reaction mixture (pH 8.5) containing 45 g of 1-(3,4-dimethoxyphenyl)-2-propanone, 28.3 g of (R)-1-phenylethylamine, and 65.0 g of oleic acid. The components were reacted at 30° C. for 39 hours. As a result, 81.6% of the substrate was converted to (R)-1-(3,4-dimethoxyphenyl)-2-aminopropane. After the pH of the reaction mixture to 2.0 with hydrochloric acid was adjusted, the reaction mixture was extracted with toluene to separate ketones by migrating the ketones to the organic layer. After the pH of the aqueous layer was adjusted to 12 with sodium hydroxide, the reaction mixture was extracted with toluene again, and 32.9 g of (R)-1-(3,4-dimethoxyphenyl)-2-aminopropane was contained in the organic layer. The separation of the desired compound from the extract was carried out by distillation. As a result, 30.3 g of (R)-1-(3,4-dimethoxyphenyl)-2-aminopropane was contained in the main distillated fraction. The total yield obtained from the sequential procedures was about 68.7%, and the optical purity was about 99.6% ee ((R)-form).

EXAMPLE 7

The Arthrobacter species KNK168 strain was subjected to shaking culture in a Sakaguchi flask containing 400 ml of the R medium at 30° C. for 30 hours. After harvesting the cells, the cells were suspended in 40 ml of a 20 mM potassium phosphate buffer (pH 6.8) containing 0.1% of 2-mercaptoethanol. After the cells were disrupted by ultrasonic sound, the precipitates were removed by centrifugation to obtain 34 ml of a cell-free extract obtained as a supernatant.

Using 10 ml of the cell-free extract, the components were reacted in 100 ml of a reaction mixture comprising a 0.1 M Tris-hydrochloric acid buffer (pH 8.5) containing 0.5 g of 1-(3,4-dimethoxyphenyl)-2-propanone and 0.34 g of (R)-1-phenylethylamine at 30° C. for 24 hours. As a result, 0.36 g of (R)-(3,4-dimethoxyphenyl)-2-aminopropane was formed.

EXAMPLE 8

The Arthrobacter species KNK168 strain was cultured in the same manner as in Example 7, and the cells were separated from 1 ml of the culture. The cells were suspended in 1 ml of a reaction mixture containing a 0.1 M Tris-hydrochloric acid buffer (pH 8.5), 40 mg of racemic 1-(3, 4-dimethoxyphenyl)-2-aminopropane, 20 mg of pyruvic acid, and 2% of sodium dodecyl sulfate. The components were reacted at 30° C. for 48 hours with stirring. As a result of the analysis of the mixture after the reaction, 20.5 mg of 1-(3,4-dimethoxyphenyl)-2-aminopropane remained, and its optical purity was 96% ee ((S)-form).

EXAMPLE 9

The Arthrobacter species KNK168 strain was cultured in 3.5 liter of the J medium at 30° C. for 43 hours using a 5 liter mini-jar in the same manner as in Example 6. The cells were harvested by centrifugation, and the harvested cells were suspended in 1 liter of 20 mM potassium phosphate buffer (pH 6.8) containing 0.01% of 2-mercaptoethanol. The cells were disrupted by Dynomill (Trade Mark, Switzerland), and 810 ml of the supernatant was separated by centrifugation. Protamine sulfate was added to this supernatant so as to give a concentration of 50 mg/ml, and nucleic acids were removed. Ammonium sulfate was added thereto so as to have a concentration of 30% to saturation, and the precipitated protein was removed. Thereafter, ammonium sulfate was added again so as to have a concentration of 60% to saturation, and the precipitated protein was separated. This protein was dissolved in the above-mentioned buffer, and it was dialyzed against the same buffer. After the composition of the buffer was adjusted to 20% (v/v) of glycerol, 0.3 M of NaCl, and 20 μM of pyridoxal phosphate, a DEAE-Sepharose, Fast-Flow (Pharmacia) column (φ4.4 cm×20 cm) was charged with the buffer, which was eluted with an NaCl linear concentration gradient of from 0.3 to 0.5 M. After this active fraction was collected and dialyzed, ammonium sulfate was added thereto so as to give a concentration of 0.2 M. A Phenylsepharose (Pharmacia) column (φ2.2 cm×17 cm) was charged with the active fraction, which was eluted with an ammonium sulfate linear concentration gradient of from 0.2 to 0 M. After the concentration of the ammonium sulfate in the active fraction was adjusted to 0.6 M, Butylsepharose (Pharmacia) column (φ2.2 cm×17 cm) was charged with the active fraction, which was eluted with an ammonium sulfate linear concentration gradient of from 0.6 to 0.2 M. The active fraction was collected and concentrated by ultrafiltration. Thereafter, the concentrated fraction was subjected to electrophoresis with SDS-polyacrylamide gel, and as a result, substantially a single band was formed at the position corresponding to a molecular weight of about 37,000.

EXAMPLE 10

The amino acid sequence in the neighborhood of the amino terminal of the purified enzyme protein obtained in Example 9 was analyzed by a Gas-Phase Protein Sequencer (470A, Applied Biosystems, Inc.). As a result, it was found that the above enzyme had an amino acid sequence of SEQ ID NO:1 in Sequence Listing:

Glu-Ile-Val-Tyr-Thr-His-Asp-Thr-Gly-Leu-Asp-Tyr in the neighborhood of the amino terminal end.

EXAMPLE 11

Using the purified enzyme obtained in Example 9, reactivities to various amino compounds when using pyruvic acid as an amino acceptor were evaluated. 150 µl of a solution of the purified enzyme diluted ten-folds was added to 150 µl of a substrate solution (0.1 M potassium phosphate buffer (pH 8.3), 40 mM pyruvic acid, 0.1 mM pyridoxal phosphate, and 40 mM various amino compounds). The components were reacted at 30° C. for 1 hour. The reaction tube was transferred into boiling water to stop the reaction, and, thereafter, a part of the reaction mixture was diluted five-folds. Ten µl of 0.1 M boric acid buffer (pH 8.0) and 20 µl of an ethanol solution of 80 mM of 4-fluoro-7-nitro-2,1, 3-benzoxadiazole (NBD-F) were added to 10 µl of the above-mentioned diluted reaction mixture. The components were reacted at 60° C. for 1 minute, and, thereafter, the reaction mixture was ice-cooled, and 460 µl of 5 mM HCl was added thereto. This reaction mixture was analyzed by high-performance liquid chromatography using fine pack C18-5 column and using a 0.1 M potassium phosphate buffer (pH 6.5) and $CH_3CN$ (90:10) as an eluent solution to detect formation of alanine-NBD using excitation wavelength of 470 nm and using detection wave of 530 mm. The results thereof are shown in Table 8 in terms of relative activity in the case of using R-1-phenylethylalanine as a substrate.

It is apparent from the Table 8 that (S)-2-phenylglycinol, 3-aminophenylbutane, and the like, showed favorable reactivities.

TABLE 8

| Compound | Relative Activity (%) |
| --- | --- |
| (R)-1-Phenylethylamine | 100 |
| (R)-3,4-Dimethoxyaminopropane | 30 |
| 1-Methylheptylamine | 47 |
| 2-Heptylamine | 37 |

TABLE 8-continued

| Compound | Relative Activity (%) |
| --- | --- |
| 1-Methylpropylamine | 1.2 |
| Benzylamine | 0.8 |
| (S)-2-Phenylglycinol | 180 |
| 3-Aminophenylbutane | 84 |
| L-Phenylalaninol | 0.8 |

EXAMPLE 12

Using the purified enzyme obtained in Example 9, reactivities to various carbonyl compounds using (R)-1-phenylethylamine as an amino donor were evaluated. 50 µl of a solution of the purified enzyme was added to 200 µl of a substrate solution (0.1 M Tris-HCl buffer (pH 8.5), 25 mM (R)-1-phenylethylamine, 0.1 mM pyridoxal phosphate, and 25 mM various carbonyl compounds), and the components were reacted at 30° C. for 1 to 3 hours. The reaction tube was transferred into boiling water to stop the reaction, and, thereafter, the reaction mixture was diluted five-folds with methanol. This diluted solution was analyzed by high-performance liquid chromatography using fine pack C18-5 column and using methanol/water (20:80) as an eluent solution to quantitatively analyze acetophenone formed by the reaction. The results thereof are shown in Table 9 in terms of relative activity in the case of using pyruvic acid as a substrate. It is apparent from the Table 9 that oxalacetic acid, phenoxy-2-propanone, and the like also showed favorable reactivities.

TABLE 9

| Compound | Relative Activity (%) |
| --- | --- |
| Pyruvic acid | 100 |
| Oxalacetic acid | 87 |
| Glyoxylic acid | 4 |
| 2-Ketobutyric acid | 7 |
| Ethyl pyruvate | 27 |
| Ethyl acetoacetate | 4 |
| 2-Decane | 3 |
| 4-Methoxyphenyl acetone | 14 |
| 1-(3,4-Dimethoxyphenyl)-2-propanone | 7 |
| Benzyl acetone | 3 |
| 4-(4-Methoxyphenyl)-2-butanone | 7 |
| 1-Phenyl-2-butanone | 1 |
| Phenyl acetaldehyde | 13 |
| Ethyl benzoyl acetate | 2 |
| Phenoxy-2-propanone | 83 |
| Diacetyl | 10 |
| 1-Methoxy-2-propanone | 16 |
| 1-Tetralone | 1 |
| 2-Acetylpyridine | 19 |
| 3-Acetylpyridine | 8 |
| 4-Acetylpyridine | 27 |
| 3-Acetoxypyridine | 1 |
| 2-Acetylpyrazine | 17 |
| 2-Acetylfuran | 2 |
| 2-Acetylthiophene | 1 |
| 2-Acetylthiazole | 10 |

EXAMPLE 13

The Arthrobacter species KNK168 strain was cultured in the same manner as in Example 7, and the cells were separated from 1 ml of the culture. The cells were suspended in 1 ml of a reaction mixture containing a 0.1 M Tris-hydrochloric acid buffer (pH 8.5), 100 mM (R)-1- phenylethylamine, 100 mM methoxy-2-propanone, and 0.1% of sodium dodecyl sulfate. The components were reacted at 30° C. for 20 hours with stirring. As a result of the analysis of the reaction mixture, methoxy-2-propanone, the substrate, almost disappeared and converted to 2-amino-1-methoxypropane, and its optical purity was 99.4% ee ((R)-form).

EXAMPLE 14

The Arthrobacter species KNK168 strain was cultured in the same manner as in Example 13, and the cells were separated from 1 ml of the culture. The cells were suspended in 1 ml of a reaction mixture containing a 0.1 M Tris-hydrochloric acid buffer (pH 8.5), 50 mg of racemic 2-amino-1-methoxypropane, 37.5 mg of pyruvic acid, and 0.1% of sodium dodecyl sulfate. The components were reacted at 30° C. for 24 hours with stirring. As a result of the analysis after the reaction, 23.4 mg of 2-amino-1-methoxypropane remained, and its optical purity was 95% ee ((S)-form).

EXAMPLE 15

By carrying out the same reaction as in Example 14 using 200 mM racemic 2-amino-1-methoxypropane, and 150 mM n-butylaldehyde or propionaldehyde, the components were reacted at 30° C. for 20 hours. As a result of the analysis thereof, the (S)-form of 2-amino-1-methoxypropane was concentrated, and the ratio of the (S)-form was 76% in a case of using n-butylaldehyde, and 58% in a case of using propionaldehyde.

EXAMPLE 16

The influence of pH on the activity was evaluated by using the purified enzyme obtained in Example 9. 0.1 ml of an enzyme solution which was diluted suitably beforehand was added to 0.9 ml of a solution containing 20 µmol of 1-(3,4-dimethoxyphenyl)-2-propanone, 20 µmol of (R)-1-phenylethylamine, and 1 µmol of pyridoxal phosphate, of which the pH was adjusted using the buffer described as follows. The components were reacted at 30° C. for 1 hour. The used buffers were an acetic acid buffer ($CH_3COONa$ being used as the abbreviation; pH 4 to 6), a potassium phosphate buffer (KPB; pH 5 to 8), and a Tris-hydrochloric acid buffer (Tris-HCl; pH 7 to 10), all of these buffers having final concentrations of 0.1 M. The formed (R)-DMA in the reaction mixture after the reaction was quantitatively analyzed by high-performance liquid chromatography. The relative activity at each pH, relative to the activity at pH 8.5 as being 100%, is shown in FIG. 1. It was found that the optimum pH of this enzyme is in the neighborhood of pH 8.5 (pH 7.5 to 9.0).

EXAMPLE 17

Figure 2:
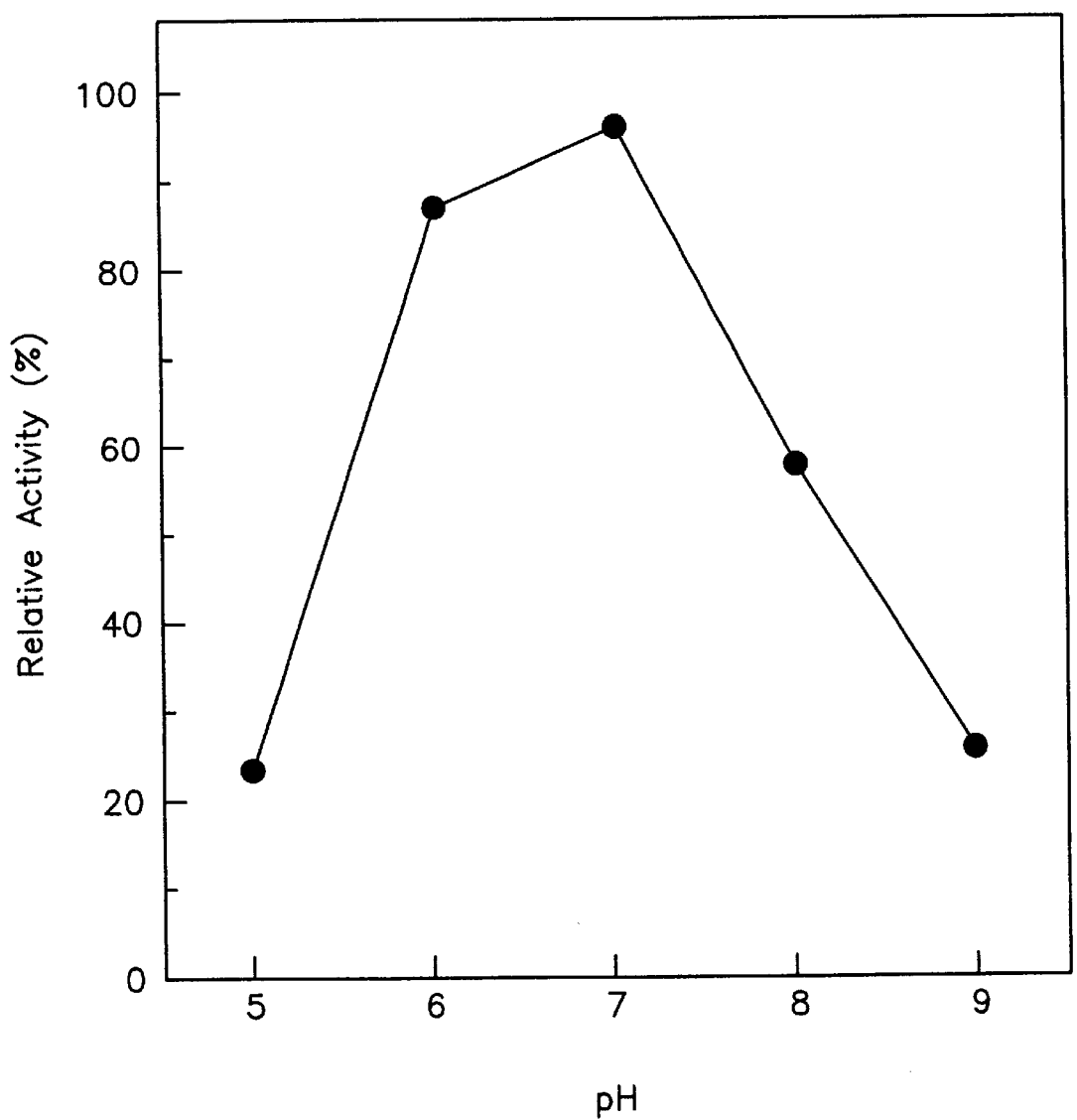
FIG. 2 is a graph showing the stable pH for the enzyme of the present invention.

The influence of the pH on the stability of the enzyme was evaluated by using the purified enzyme obtained in Example 9. After the pH of the enzyme solution was adjusted by HCl or NaOH, the reaction mixture was incubated at 20° C. for 23 hours. Thereafter, in the same manner as in Example 16, the components were reacted at pH 8.5, and the formed (R)-DMA was quantitatively analyzed. The results in which the relative activities of the treated samples at each pH, relative to the activity of the untreated enzyme solution as being 100%, are shown in FIG. 2. It was found that this enzyme was most stable at a pH in the neighborhood of 7.

EXAMPLE 18

The Arthrobacter species KNK168 strain was subjected to shaking culture in the same manner as in Example 6 using (RS)-1-methylpropylamine as an enzyme inducer. The cells harvested from one liter of the culture were suspended in one liter of a 0.1 M Tris-hydrochloric acid buffer (pH 8.5), and 30 g of 1-(3-trifluoromethylphenyl)-2-propanone, 18 g of (R)-1-phenylethylamine, and 44 g of oleic acid were added thereto. The components were reacted at 30° C. for 40 hours with stirring. After the reaction, the resulting mixture was subjected to extraction and distillation in the same manner as in Example 6, to give 19.5 g of (R)-1-(3-trifluoromethylphenyl)-2-aminopropane. The optical purity was 100% ee, and the yield was 65%.

INDUSTRIAL APPLICABILITY

According to the present invention, it is made possible to easily prepare at a high yield the optically active (R)-amino compounds and the like having an aryl group and the like at their 1-position, which have been conventionally difficult to prepare.

IDENTIFICATION OF DEPOSITED MICROORGANISM (1) Name and Address of Depository Organization The Ministry of International Trade and Industry, National Institute of Bioscience and Human-Technology, Agency of Industrial Science and Technology 1-3, Higashi 1-chome, Tsukuba-shi, Ibaraki-ken, Japan (zip code 305)

(2) Date of Deposit Sep. 8, 1995 (date of original deposit)

(3) Accession Number FERM BP-5228

---

---

What is claimed is:

1. A method for preparing an optically active (R)-amino compound comprising the step of stereoselectively carrying out amino group transfer by action of an (R)-form-specific transaminase in the co-presence of a ketone compound (amino acceptor) and an amino compound (amino donor), wherein said amino acceptor is a compound represented by the following general formula (I):

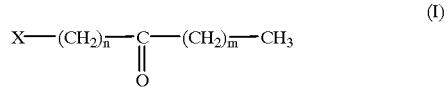

wherein n is 0 to 5; m is 0 or 1; and X represents an unsubstituted aryl group having 6 to 14 carbon atoms; an aryl group having 6 to 14 carbon atoms and having one or more substitutents selected from the group consisting of an alkyl group having 4 to 15 carbon atoms, a hydroxyl group, a fluorine atom, a chlorine atom, a bromine atom, an iodine atom, a nitro group, a carboxyl group, and a trifluoromethyl group; a substituted phenyl group selected from the group consisting of 2-methoxyphenyl, 3-methoxyphenyl, 4-methoxyphenyl, 2,4-dimethoxyphenyl, 3,4-dimethoxyphenyl and 3-trifluoromethylphenyl; a methoxyl group; a pyridyl group; a pyrazinyl group; a thienyl group; a furyl group; or a thiazolyl group; and wherein said amino donor is a compound of an achiral form, a racemic form, or an (R)-form represented by the general formula (II):

wherein $X_1$ and $X_2$ independently represent a hydrogen atom; a straight-chain alkyl group having 1 to 10 carbon atoms; a branched alkyl group having 5 to 12 carbon atoms; an unsubstituted aryl group having 6 to 14 carbon atoms; an aryl group having 6 to 14 carbon atoms and having one or more substitutents selected from the group consisting of an alkyl group having 1 to 4 carbon atoms, a hydroxyl group, a fluorine atom, a chlorine atom, a bromine atom, an iodine atom, a nitro group, and a carboxyl group; an aralkyl group having 7 to 16 carbon atoms and having one or more substitutents selected from the group consisting of an alkyl group having 1 to 4 carbon atoms, a hydroxyl group, a fluorine atom, a chlorine atom, a bromine atom, an iodine atom, a nitro group, and a carboxyl group; or a hydroxymethyl group, thereby giving an optically active (R)-amino compound represented by the general formula (IV):

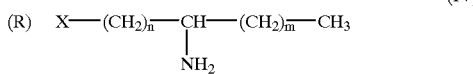

wherein n, m, and X have the same definitions as those of n, m, and X in the general formula (I), respectively.

2. The method for preparing an optically active (R)-amino compound according to claim 1, wherein in the general formula (II), $X_1$ is an alkyl group having 2 to 10 carbon atoms, a phenyl group, or a naphthyl group, and $X_2$ is an alkyl group having 1 or 2 carbon atoms.

3. The method for preparing an optically active (R)-amino compound according to claim 1, wherein the amino donor is (R)-1-phenylethylamine, (R)-1-naphthylethylamine, (R)-1-methylpropylamine, (R)-2-aminopentane, (R)-2-amino-1-propanol, (R)-1-methylbutylamine, (R)-1-phenylmethylamine, (R)-1-amino-1-phenylethanol, (R)-2-amino-2-phenylethanol, (R)-3-aminoheptane, (R)-1-amino-3-phenylpropane, (R)-2-amino-4-phenylbutane, (R)-2-amino-3-phenylpropanol, (R)-3,4-dimethoxyaminopropane, (R)-1-methylheptylamine, benzylamine, (S)-2-phenylglycinol-3-aminophenylbutane, L-phenylalaninol, (R)-2-amino-1-methoxypropane, or a racemic compound thereof.

4. The method for preparing an optically active (R)-amino compound according to claim 1, wherein in the general formula (I) and the general formula (IV), n and m are n=1 and m=0.

5. The method for preparing an optically active (R)-amino compound according to claim 1, wherein the amino acceptor and the amino donor are brought into contact with a culture of microorganisms, separated bacterial cells, treated bacterial cells, or immobilized bacterial cells which produce (R)-form specific transaminases.

6. The method for preparing an optically active (R)-amino compound according to claim 1, wherein the amino acceptor and the amino donor are brought into contact with cell-free extracts of microorganisms, crudely purified enzymes, purified enzymes, or immobilized enzymes which produce (R)-form specific transaminases.

7. The method for preparing an optically active (R)-amino compound according to claim 1, wherein the microorganism for producing the transaminase is a microorganism belonging to the genus Arthrobacter.

8. The method for preparing an optically active (R)-amino compound according to claim 7, wherein the microorganism belonging to the genus Arthrobacter is Arthrobacter species (Arthrobacter sp.) KNK168 (FERM BP-5228).

9. The method for preparing an optically active (R)-amino compound according to claim 1, wherein when culturing the microorganism for producing the transaminase, one or more members selected from the group consisting of (RS)-1-methylpropylamine, (RS)-1-phenylethylamine, (RS)-1-methylbutylamine, (RS)-3-amino-2,2-dimethylbutane, (RS)-2-amino-1-butanol, and (R)- or (RS)-1-(3,4-dimethoxyphenyl)aminopropane are added to a medium as an inducer for the enzyme.

10. The method for preparing an optically active (R)-amino compound according to claim 1, wherein a reaction at a pH of not less than 5 and not more than 12 is carried out in the amino group transfer reaction.

11. The method for preparing an optically active (R)-amino compound according to claim 1, wherein a surfactant or a fatty acid is added as a reaction accelerator upon reaction in the amino group transfer reaction.

12. A method for preparing an optically active (S)-amino compound, comprising the step of stereoselectively carrying out amino group transfer reaction by action of an (R)-form-specific transaminase to an amino compound of a racemic form represented by the general formula (V) in the presence of a ketone compound (amino acceptor) represented by the general formula (III), to give an optically active (S)-amino compound represented by the general formula (VI):

-continued (RS) 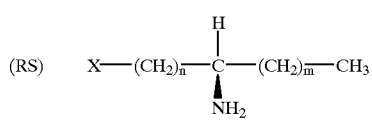

(V)

(S) 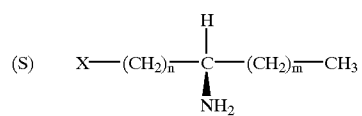

(VI)

wherein $X_1$ and $_2$ independently represent a hydrogen atom; a straight-chain alkyl group having 1 to 10 carbon atoms; a branched alkyl group having 5 to 12 carbon atoms; an unsubstituted aryl group having 6 to 14 carbon atoms; an aryl group having 6 to 14 carbon atoms and having one or more substituents selected from the group consisting of an alkyl group having 1 to 4 carbon atoms, a hydroxyl group, a fluorine atom, a chlorine atom, a bromine atom, an iodine atom, a nitro group, and a carboxyl group; an aralkyl group having 7 to 16 carbon atoms and having one or more substituents selected from the group consisting of an alkyl group having 1 to 4 carbon atoms, a hydroxyl group, a fluorine atom, a chlorine atom, a bromine atom, an iodine atom, a nitro group, and a carboxyl group; or a hydroxymethyl group or a hydroxyethyl group; and wherein n is 0 to 5; m is 0 or 1; and X represents an unsubstituted aryl group having 6 to 14 carbon atoms; an aryl group having 6 to 14 carbon atoms and having one or more substituents selected from the group consisting of an alkyl group having 4 to 15 carbon atoms, a hydroxyl group, a fluorine atom, a chlorine atom, a bromine atom, an iodine atom, a nitro group, a carboxyl group, and a trifluoromethyl group; or a methoxyl group.

* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Arthrobacter sp.

<400> SEQUENCE: 1

Glu Ile Val Tyr Thr His Asp Thr Gly Leu Asp Tyr
 1               5                  10